(12) United States Patent
Cornsweet

(10) Patent No.: US 6,836,337 B2
(45) Date of Patent: Dec. 28, 2004

(54) NON-INVASIVE BLOOD GLUCOSE MONITORING BY INTERFEROMETRY

(75) Inventor: Tom N. Cornsweet, Prescott, AZ (US)

(73) Assignee: Visual Pathways, Inc., Prescott, AZ (US)

( * ) Notice: Subject to any disclaimer, the term of this patent is extended or adjusted under 35 U.S.C. 154(b) by 0 days.

(21) Appl. No.: 10/247,753

(22) Filed: Sep. 19, 2002

(65) Prior Publication Data

US 2003/0076508 A1 Apr. 24, 2003

Related U.S. Application Data

(60) Provisional application No. 60/323,939, filed on Sep. 20, 2001.

(51) Int. Cl.[7] .................................................. G01B 9/02
(52) U.S. Cl. ....................................... 356/517; 356/450
(58) Field of Search ................................. 356/450, 517, 356/481

(56) References Cited

U.S. PATENT DOCUMENTS

| | | | |
|---|---|---|---|
| 4,653,855 A | | 3/1987 | Birnbach et al. |
| 5,064,286 A | * | 11/1991 | Ai et al. ....................... 356/153 |
| 5,710,630 A | * | 1/1998 | Essenpreis et al. .......... 356/479 |
| 5,896,198 A | * | 4/1999 | Chou et al. ................... 356/484 |
| 5,923,425 A | * | 7/1999 | Dewa et al. .................. 356/520 |
| 6,327,037 B1 | * | 12/2001 | Chou et al. ................... 356/484 |

OTHER PUBLICATIONS

Jongsma F.H.M. et al., "Review and Classification of Corneal Topographers", Lasers Med Sci, 1999, vol. 14, pp. 2–19.

Saloma Caesar et al., "Refractive–index measurement at high spatial resolution by source doubling", Optical Society of America, vol. 19, No. 14, Jul. 15, 1994, pp. 1088–1090.

* cited by examiner

Primary Examiner—Zandra V. Smith
Assistant Examiner—Andrew H. Lee
(74) Attorney, Agent, or Firm—Cahill, von Hellens & Glazer P.L.C.

(57) ABSTRACT

The glucose concentration in the bloodstream is directly correlated to the concentration of glucose in the aqueous humor. Furthermore, variation in the glucose concentration in the aqueous humor will cause like variations in its index of refraction. Thus, by measuring the refractive index of the aqueous humor, the glucose concentration in the blood can be determined.

The refractive index of the aqueous humor can be measured by interferometry. In various embodiments of the invention that employ interferometry, two beams may be directed onto the eye and caused to interfere, thereby producing a fringe pattern. The fringe pattern may be analyzed to determine the index of refraction of the aqueous humor in the eye and the glucose concentration therein. The glucose level in the blood can be ascertained from this information.

17 Claims, 9 Drawing Sheets

US 6,836,337 B2

NON-INVASIVE BLOOD GLUCOSE MONITORING BY INTERFEROMETRY

RELATED APPLICATION

This application claims priority under 35 U.S.C. § 119(e) from U.S. Provisional Patent Application No. 60/323,939, filed Sep. 20, 2001, entitled "Non-Invasive Blood Glucose Monitoring by Interferometry", which is hereby incorporated herein by reference in its entirety.

BACKGROUND OF THE INVENTION

1. Field of the Invention

The present invention is directed to glucose monitoring, and more specifically, to apparatus and methods for monitoring glucose using interferometry.

2. Description of the Related Art

Diabetics are advised to closely monitor the concentration of glucose in their bloodstream. If the concentration is outside of a normal healthy range, the patient needs to adjust his or her insulin dosage or sugar intake to counter the risk of diabetic complications. Current monitoring methods involve drawing blood from the patient several times a day, which is costly, painful, and poses the risk of infection. As a result, many diabetics test their blood glucose less frequently than would be desirable, increasing the possibility of diabetic related health problems. Thus, what is needed is a painless, non-invasive approach for determining the glucose level within the bloodstream.

SUMMARY OF THE INVENTION

One aspect of the invention comprises a method of measuring glucose levels in blood of a living being having an eye. The eye comprises a cornea and a lens, which together form an anterior chamber. The eye further comprises an iris and aqueous humor in the anterior chamber of the eye. The aqueous humor has an index of refraction that is correlated to the glucose level in the blood. To measure the glucose levels in the blood, two substantially coherent beams of light are propagated through the cornea to illuminate a region of the iris. The two substantially coherent beams of light propagate through the aqueous humor to reach the iris. The two beams are overlapped on the region of the iris. These two beams are sufficiently coherent so as to produce an interference pattern in this region of the iris where they overlap. The interference pattern comprises a plurality of fringes having a spatial arrangement that depends on the index of refraction of the aqueous humor. The interference pattern is imaged onto a light sensitive optical detector, and the glucose level in the blood is determined from the spatial arrangement of the fringes in the interference pattern.

Another aspect of the invention comprises an apparatus for monitoring glucose fluctuations by measuring optical properties of an eye. The apparatus comprises a light source which emits a beam of light, an optical element, an optical detector and imaging optics. The optical element is situated to receive this beam of light from the light source and to split the beam of light into first and second probe beams that propagate along respective first and second optical paths. The apparatus further includes at least one optical element in one of the optical paths to alter the optical path such that first and second probe beams intersect at a target plane. The optical detector and imaging optics are arranged to image the target plane onto the optical detector.

Another aspect of the invention comprises a method of monitoring glucose levels in blood of a living being having an eye. In this method, light is propagated through a portion of the eye comprising aqueous humor having an index of refraction that varies with glucose concentration. Phase information associated with the light is obtained through optical interference. The phase information depends at least in part on the index of refraction of the aqueous humor. The phase information is used to determine the glucose levels in the blood.

Yet another aspect of the invention comprises an alignment apparatus for lateral aligning an eye with respect to the apparatus. The apparatus comprises a central light source, a partially reflecting concave mirror, and first and second offset light sources. The partially reflecting concave mirror has an optical axis passing therethrough. The central light source is centrally disposed along this optical axis such that at least a portion of the light from the central light source propagates through the partially reflecting concave mirror along the optical axis. The first and second offset light sources are disposed in a plane passing through the optical axis. The first and second offset light sources are on opposite sides of the optical axis and emit light at an oblique angle toward the optical axis.

Still another aspect of the invention comprises an method of aligning a device with respect to a cornea wherein the cornea has a substantially spherical curvature defined by a center of curvature. In this method light is propagated toward the cornea. This light has substantially spherical wavefronts defined by a center of curvature that is substantially coincident with the center of curvature of the cornea. A portion of the light from the cornea is retrorefect, collected, and focusing onto an optical detector having a photosensitive area. When the center of curvature of the wavefronts is substantially coincident with the center of curvature of the eye, the light focused on the photosensitive area has a different intensity than when the respective centers of curvature are non-coincident.

DETAILED DESCRIPTION OF THE PREFERRED EMBODIMENT

These and other embodiments of the present invention will also become readily apparent to those skilled in the art from the following detailed description of the preferred embodiments having reference to the attached figures, the invention not being limited to any particular embodiment(s) disclosed. Accordingly, the scope of the present invention is intended to be defined only by reference to the appended claims.

Figure 1:
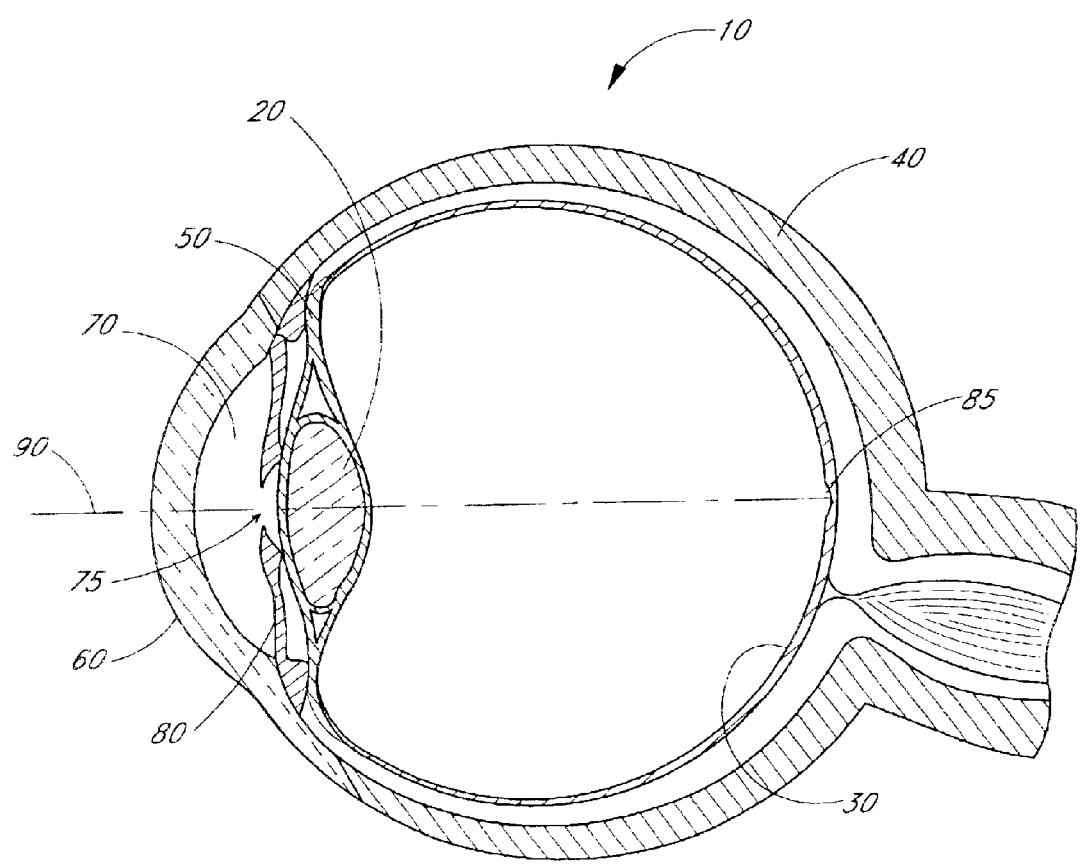
FIG. 1 is a schematic illustration of the anatomy of the eye including the cornea, iris, lens, and anterior chamber containing aqueous humor.

As is well known and illustrated in FIG. 1, an eye 10 includes a lens 20 for imaging onto a retina 30 located at the back of the eyeball. Dense relatively opaque tissue, the sclera 40, together with a curved transparent window, the cornea 60, forms a chamber inside of which is the ocular lens 20. This lens 20 is held in place by the ciliary body 50 and fibrous muscle included therewith. An iris 80 comprising opaque diffusely reflecting tissue that includes a central opening, i.e., the pupil 75, lies on an anterior surface of the lens 20. The refractive powers of the lens 20 and the cornea 60 combine to focus light on the retina 30. A tiny region approximately at the center of the retina 30 known as the fovea 85, comprises densely packed photoreceptor, which provides vision for fine detail. When the eye 10 peers at a distant object, such as for example a star, the eye 10 rotates until an image of the distant object falls on the fovea 85. A straight line drawn through the center of the pupil 75 and the fovea 85 is known as the visual axis 90, sometimes referred to as the line of sight. The cornea 60 and the lens 20 together form a cavity 70 called the anterior chamber 70. The anterior chamber 70 is filled with a transparent liquid known as aqueous humor.

Advantageously, the glucose concentration in the aqueous humor closely tracks the glucose concentration in the bloodstream to within a delay of only minutes. Increases in the glucose level of the blood are mimicked by proportional rises in the glucose level in the aqueous humor. Accordingly, by monitoring the glucose concentration of the aqueous humor, changes in the glucose concentration in the blood can be sensed.

Fluctuations in the glucose concentration of the aqueous humor have also been shown to produce a corresponding shift in the index of refractive of the aqueous humor. Therefore, devices and methods for measurements of the refractive index of the aqueous humor can be used to quantify variations in the concentration of glucose in the aqueous humor. By measuring this aqueous glucose concentration in this manner, patients can determine the concentration of glucose in the blood and adjust their insulin and sugar intake accordingly.

Interferometry can be employed to measure the index of refraction of the aqueous humor. Other optical methods can be used that monitor optical properties that are dependant on the refractive index of this fluid in the eye 10. Identifying and quantifying fluctuations in the index of refraction of the aqueous humor using light is preferred as it is clean, non-invasive, and relatively precise. Interferometers offer one approach for optically determining the refractive index of the aqueous humor, however, other well known techniques as well as those yet devised are possible alternatives.

Figure 2:
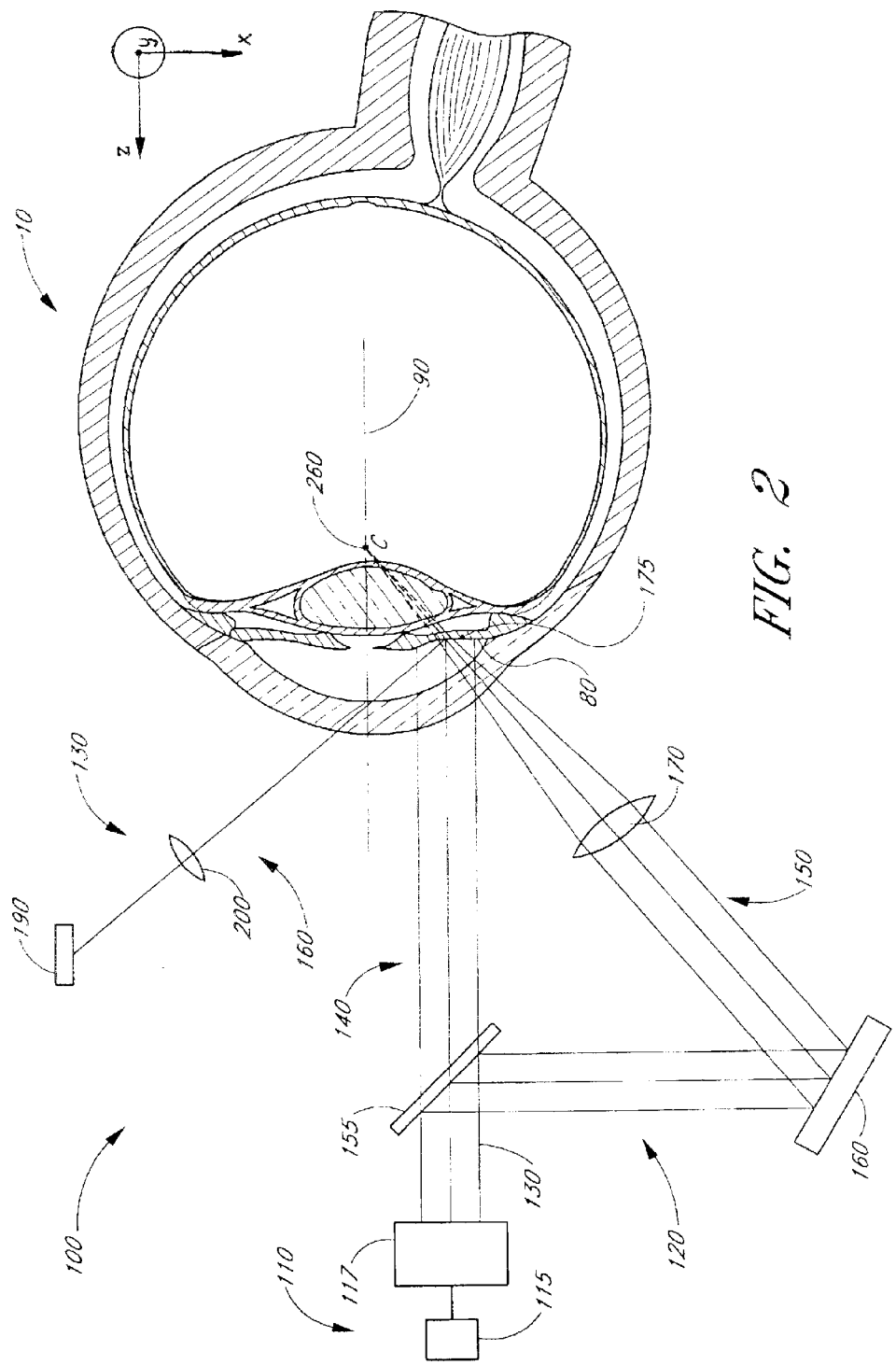
FIG. 2 schematically illustrates a device for measuring the concentration of glucose in the bloodstream of a subject by measuring optical properties of the aqueous humor within the eye.

An optical instrument 100 for measuring the refractive index of the aqueous humor is schematically illustrated in FIG. 2. This optical instrument 100 comprises a light source 110, an interferometer 120, and a detection system 130. The light source 110 preferably comprises a coherent source 115 such as a laser. This light source 110 preferably outputs invisible radiation such as infrared but is not limited to any particular wavelength range. The wavelength of the light may, for example, be between about 500 to 950 nanometers (nm). Other types of light sources may also be used.

The light source 110 may further include beam shaping optics 117 for producing a beam 130 possessing suitable properties such as intensity and diameter. In one preferred embodiment, the beam shaping optics 117 includes a beam expander. An exemplary beam expander comprises an afocal system similar to a telescope in which a substantially collimated input beam entering the beam expander exits with substantially the same degree of collimation, but with a diameter different from that of the input beam. The beam expander may increase or decrease the diameter of the beam 130 depending on the desired spatial extent and the beam size of the coherent source 115. The beam shaping optics 117 may further include a neutral density filter as well as possibly polarizers and apertures to suite the particular application. Other optics may be included in the beam shaping optics 117 and elsewhere in the instrument 100.

The interferometer 120 comprises two arms, a first and second with corresponding first and second probe beams 140, 150 that are interfered. The interferometer 120 includes a beamsplitter 155 which splits the optical beam 130 from the light source 110 into the two probe beams 140, 150. Other methods and devices (such as, other splitters comprising for example a prism) may also be employed for creating the two probe beams 140, 150 from the original beam 130. Since the first and second probe beams 140, 150 are interfered, the coherent light source 115 preferably has a coherence length that is longer than the optical path length difference between the two optical paths 140, 150. A relatively long coherence length may advantageously increase the optical contrast of the resultant interference pattern.

The inteferometer 120 further comprises optics, such as a mirror or reflector 160 and a lens 170 to direct light in the second probe beam 150 towards the eye 10 and to focus this beam. The lens 170 causes the beam 150 to be converging when incident on the eye 10, which in certain embodiments is beneficial; such a configuration, however, is not required and may vary in other designs. The use of the mirror 160 in FIG. 2 is illustrative of a preferred embodiment for directing light and should not be construed as limiting since other optical components and configurations may be used. For example, a different number of mirrors or reflectors may otherwise be employed.

The interferometer 120 is preferably adjusted such that the first probe beam 140 and the second probe beam 150 are incident on the eye 10 and, more particularly, overlap each other over a region 175 of the iris 80. A fringe pattern is formed where the two beams 140, 150 overlap.

The detection system 130 in the instrument 100 comprises an optical sensor 190 and an imaging element 200 such as a lens. In one preferred embodiment, the lens 200 has a power and is positioned appropriately to produce an image of the iris 80 on the optical detector 190.

Preferably, the principle plane of the imaging lens 200 is oriented at an angle to satisfy the Scheimpflug condition. The Scheimpflug condition is met when three lines through the plane of the iris 80, the principle plane of the imaging lens 200, and the plane of the sensor 190 all intersect at a common point. Under these circumstances, in theory all the points in the plane of the iris 80 may be simultaneously focused in the plane of the sensor 190 by the imaging lens 200.

In certain preferred embodiments, the optical sensor 190 comprises a one or two dimensional sensor array such as a charge coupled device (CCD) or a complementary metal oxide semiconductor (CMOS) detector array. Other types of optical detectors 190 may also be used. In certain embodiments, the sensor 190 produces an image signal that is received by a computer and/or other electronics for processing the image signal.

In one preferred embodiment, an image is obtained of the interference fringes formed in the region 175 in the iris 80 where the first and second beams 140, 150 intersect. The interference fringes formed on the iris 80 in the region 175 are produced due to mutual coherence of the two intersecting probe beams 140, 150. Phase differences resulting from the optical path difference traveled by the first and second probe beam 140, 150 cause constructive and destructive interference which varies with position within the overlap region 175. Consequently, bright and dark regions, i.e., a fringe pattern, are produced in the overlap region 175 on the iris 80.

As stated previously, variations in the glucose concentration of the aqueous humor alter the refractive index of the aqueous humor 20. Since the probe beams 140, 150 both pass through the aqueous humor, the interference fringes formed on the iris 80 are affected by changes in the refractive index of the aqueous humor. More particularly, the optical path length of the first and second probe beams 140, 150 varies with the index of refraction of the aqueous humor in the anterior chamber 70 of the eye 10. The fringe pattern varies as well. Thus, variations in the glucose concentration of the aqueous humor are directly correlated to quantitative changes in the fringes formed on the iris 80 in the overlap region 175.

Figure 3A:
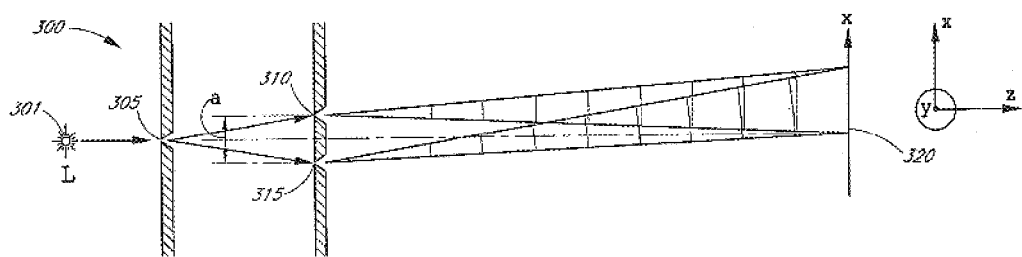
FIGS. 3A and 3B schematically illustrates the interference of two cylindrical wavefronts produced by Young's double slit configuration.
Figure 3B:
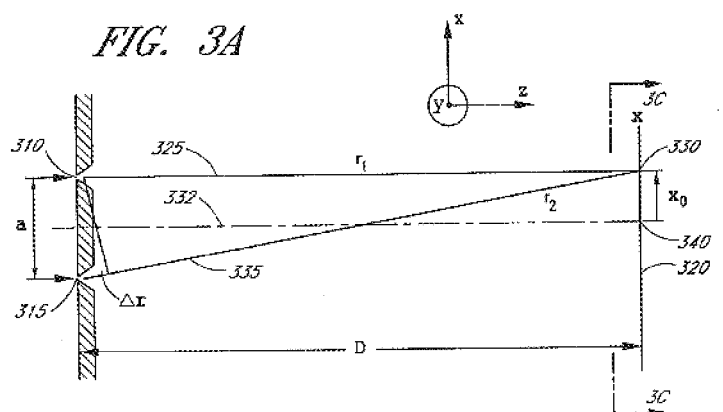
Figure 3C:
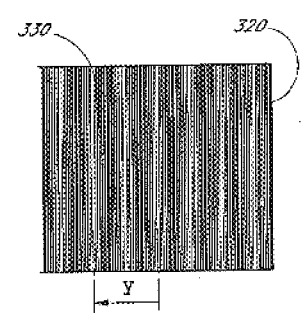
FIG. 3C is an exemplary interference pattern comprising a plurality of fringes resulting from the interference of the two cylindrical wavefronts produced in the configuration schematically illustrated in FIGS. 3A and 3B.

The nature of the fringes formed on the iris 80 may be generally understood by reference to FIGS. 3A–3C, which schematically illustrate the formation of interference fringes using Young's double slit configuration 300. In this optical arrangement, a monochromatic light source 301 emits light that is transmitted through a narrow vertically oriented elongated slit 305, which diffracts the light incident thereon. The result is an optical beam having cylindrical wavefronts. These cylindrical wavefronts illuminate two other vertically oriented elongated slits 310, 315 which are laterally (i.e., horizontally) separated from each other by a distance a. Light is diffracted by the two slits 310, 315, the output of which is a pair of beams also characterized by vertically oriented cylindrical wavefronts. The two beams illuminate a diffuse screen 320 where they interfere constructively and destructively producing vertical fringes such as the ones schematically illustrated in FIG. 3C.

The cause of the elongated bright and dark regions in FIG. 3C has been well characterized and may be understood as follows. Constructive or destructive interference results when the two beams are overlapped. The interference at a given location on the diffuse screen 320 is determined by the respective optical path distance from the two slits 310, 315 to that specific location on the diffuse screen. For example, a ray 325 shown in FIG. 3B that is transmitted through the first slit 310, travels a distance $r_1$, and illuminates the diffuse screen 320 at a point 330, which is located a distance $\chi_0$ from a centerline 332. The centerline 332 through the system is defined as a line normal to the diffuse screen 320 that bisects the two slits 310, 315. The distance from the diffuse screen 320 to the plane containing the two slits 310, 315 is defined as D. A second ray 335 is transmitted through the second slit 315, travels a distance $r_2$, and illuminates the diffuse screen 320 at the same point 330. The distances through which the two rays travel may differ, as indicated in FIG. 3B, by the distance $\Delta r = r_1 - r_2$. If the original slit 305 is sufficiently narrow, the light emerging from it (in the x-z plane) is substantially coherent and the waves associated with rays produced by the light source 301 oscillate in phase with one another. The phase of the two rays 325, 335 at the point 330 on the screen 320 is determined in part by the respective path lengths $r_1$ and $r_2$. More particularly, the relative phase between the two rays 325, 335 is proportional to the difference in the two path lengths, i.e., $\Delta r$. If the two rays 325, 335 have the same intensity $I_1 = I_2 = I_0$, then the intensity at the point 330 is given by the well known relation, $$I = I_0(1 + I_0 \cos(\delta)) \qquad (1)$$

where $I_0$ is the intensities of rays 325, 335 and $\delta$ the relative phase between the rays 325, 335 given by the relation ($\delta = 2\pi \Delta r / \lambda$), where $\lambda$ is the wavelength of the source 301. In this case, the light emitted from the slits 310, 315 propagates though air or vacuum to the diffusely reflecting screen 320.

Accordingly, if for example the distance $\Delta r$ corresponds to an optical path difference over which light at the wavelength $\lambda$ oscillates through precisely one-half of a cycle ($\pi$ radians in phase), then the two rays 325, 335 will be $\pi$ radians out of phase with each other at point 330 and the two rays 325, 335 will cancel each other, resulting in a reflected intensity of zero at point 330. If $\Delta r$ is exactly an integer number of cycles (i.e., an integer multiple of $2\pi$ radians), the two rays will be in phase at the point 330, and under ideal conditions, the resulting reflected intensity will equal the sum of the intensities of the two individual rays.

For points 330 on the screen 320 closer to the centerline 332 (i.e., for smaller values of x), $\Delta r$ is reduced, reaching a value of zero at a center point 340 where the centerline intersects the screen. The optical path difference $\Delta r$ increases again for positions below the centerline (i.e., negative values on the x-axis). The intensity on the screen 320 oscillates between high and low on both sides of the centerline 332 as illustrated in FIG. 3C. Specifically, the reflected intensity I fluctuates along the diffusing surface 320 accordingly to the relation, $$I = 4A_0 \cos^2[\alpha \pi \chi / (D \lambda)] \qquad (2)$$

where $A_0$ is the amplitude of the rays 325, 335 at the diffuse screen 320, $\chi$ is the distance along the x-axis across the diffuse screen 320 as measured from the centerline 332 where x=0, $\alpha$ is the lateral distance separating the two slits 310, 315, D is the distance from the diffuse screen 320 to the plane containing the two slits 310, 315, and $\lambda$ is the wavelength of the source 301. Since the difference in path lengths, $\Delta r$, is substantially the same for the plurality of points on the screen 320 in the ±y-direction, the interference fringes produced by the elongated slits 310, 315, which are oriented lengthwise parallel to the y-axis, are linear and also oriented along the y-direction.

The relations derived based on FIGS. 3A and 3B assume that the region between the slits 310, 315 and the diffuse screen 320 is filled with air or vacuum. Constructive or destructive interference, however, does not depend solely on the distance traveled by the light and, more specifically, the difference in the distance between the two physical paths, Δr. Rather, the time it takes the light to travel through that optical path difference determines the result of the interference. The phase of the light depends upon time, not distance. Accordingly, the index of refraction of the medium through which the light propagates along the optical paths will affect the resultant fringe pattern as the refractive index determines the phase of the light.

If the region between the slits 310, 315 and the diffuse screen 320 is filled, instead, with a liquid such as water, the velocity of the light waves is reduced. The index of refraction of water is 1.5. Accordingly, the speed of light in the region between the slits 310, 315 and the diffuse screen 320 is approximately three quarters of that in air. Under these conditions, the value of Δr between two rays transmitted from slits 310, 315 will produce a phase difference that is 4/3 larger than when the region between the slits 310, 315 and the diffuse screen 320 is filled with air. Likewise, there will be 4/3 as many fringes per unit distance formed on the diffuse screen 320 than when the region between the slits 310, 315 and the diffuse screen 320 is filled with air. The number of fringes per unit distance across the screen 320 is therefore directly proportional to the speed of light in the medium. In certain embodiments, this relationship between refractive index of a media and the spacing between fringes may be used to determine the refractive index of that media. Other effects on the fringe pattern can also be measured and quantified to determine the index of refraction of the medium.

Referring again to FIG. 2, light from light source 115 is transmitted through the beam shaping optics 117 and is incident on the beamsplitter 155. A fraction of the light is transmitted through the beamsplitter 155 to produce the first probe beam 140. This probe beam 140 is preferably substantially parallel to the visual axis 90 of the eye 10. When light from the probe beam 140 illuminates the cornea 60, the light is refracted toward the pupil 75 and illuminates the iris 80.

Another fraction of the light, i.e., the remainder, is reflected from the beamsplitter 155 forming the second probe beam 150. In certain embodiments, the fraction of the light that is transmitted through the beamsplitter 155 to produce the first probe beam 140 and the fraction of light is reflected by the beamsplitter 155 to produce the second probe beam 150 are selected so that they have substantially equal intensity when they are interfered on the front surface of the iris 80. Favorable contrast can thereby be achieved.

This reflected beam 150 is directed by the mirror or reflector 160 through the focusing lens 170 towards the eye 10. In certain embodiments, the focal length of the lens 170 is substantially equal to the distance from the focusing lens 170 to a point 260 located at the center of curvature, C of the front corneal surface of the cornea 60. The light transmitted through the lens 170 converges toward the center point 260 however is incident on the cornea 60 before reaching its center, C. As discussed above, the focal length of the focusing lens 170 is preferably selected to substantially correspond to the distance from the lens to the radius of curvature of the cornea 60. When this condition is satisfied and the lens 170 is positioned such that its focal point and this center of curvature are coincident, then the rays associated with the second beam 150 that are incident on the corneal surface will be substantially perpendicular thereto. With an angle of incidence of substantially zero, the converging rays are not refracted by the cornea 60.

Figure 4:
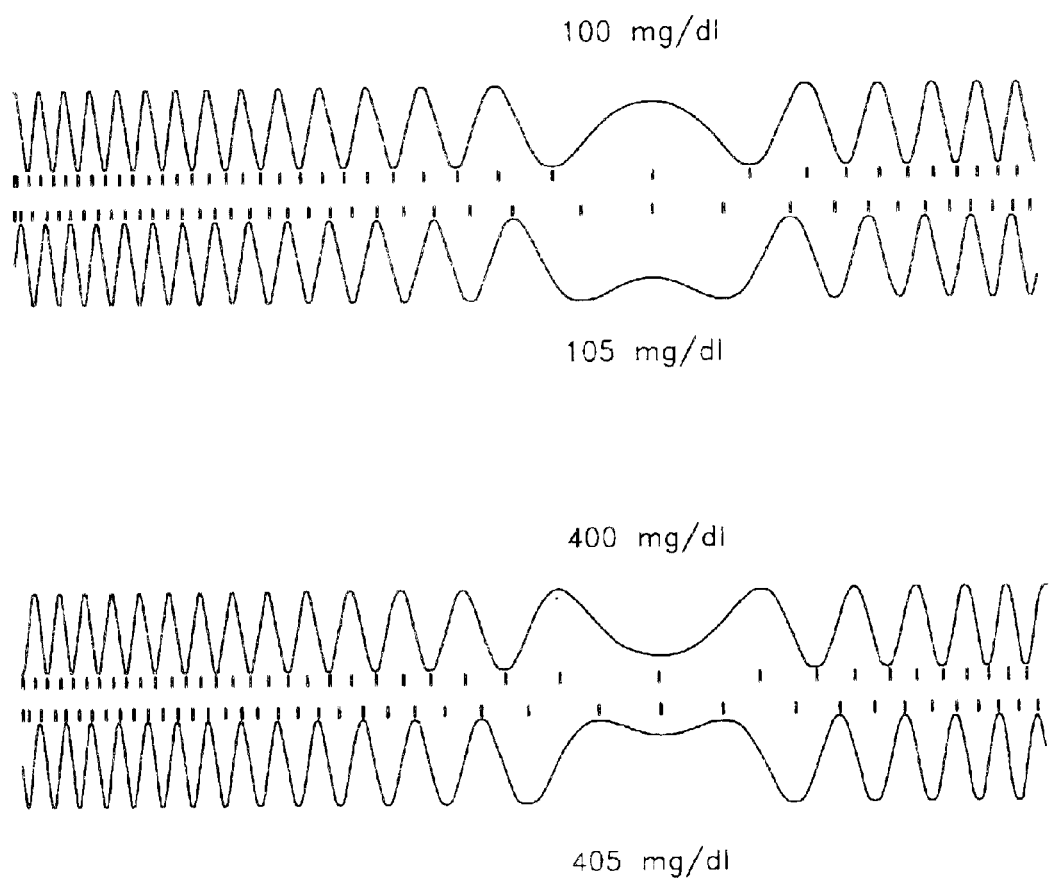
FIG. 4 shows profiles of the fringe patterns obtained using the device schematically illustrated in FIG. 2 for four different aqueous glucose concentrations.

As discussed above, the converging rays associated with this second probe beam 150 preferably illuminate a substantially similar region 175 of the iris 80 as the first probe beam 140. The overlap of the two beams 140, 150 produces interference fringes on the iris 80 as a consequence of constructive and destructive interference. The interference process is generally similar to the optical phenomena related to the Young's double slit configuration 300 discussed above with reference to FIGS. 3A–3C. The configuration in FIGS. 3A and 3B, however, differs from the interferometer 120 shown FIG. 2. The fringes formed in the Young's double slit configuration 300 were produced by two probe beams each having cylindrical wavefronts defined by substantially equal radii of curvature. The first and second probe beams 140, 150 in the inteferometer 120 depicted in FIG. 2 comprise wavefronts having different radii of curvature. In various preferred embodiments, first probe beam 140 is has a radius of curvature of about 25 millimeter. The refractive power of the cornea 60 will cause the probe beam 140 to be convergent such that spherical wavefronts are incident on the iris 80. At the iris 80, the second probe beam 150 also comprises substantially spherical wavefronts. These spherical wavefronts are defined by a radius of curvature that is approximately equal to the distance from the focusing lens 170 to the center of curvature 260 of the cornea 60. The result of interfering substantially planar waves with substantially spherical wavefronts is a plurality of annular shaped fringes. In various preferred embodiments, the overlap region 175 corresponds to a portion of these annular shaped fringes. Accordingly, the fringes may not be complete rings but only portions of annuli. An intensity profile across a cross-section of these fringes corresponding, for example, to the x-z plane is shown in FIG. 4. These fringes in FIG. 4 are for a variety of glucose concentrations and respective refractive index values. As shown, these fringe patterns have a point of symmetry and the frequency of the fringes increases to either side of the point of symmetry with distance away from the point of symmetry.

FIG. 4 shows profiles of the fringe patterns for four different aqueous glucose concentrations. Short vertical lines are included to mark the locations of the peaks and troughs in the interference pattern. Differences in the refractive index between the aqueous humor solutions shown in the different profiles produce variation in the plot pattern. For example, the shape of the profile in the region near the point of symmetry as well as the rate of change of fringe spacing varies. In contrast, the location of the point of symmetry is substantially fixed over a wide range of refractive indices.

An analytical expression can be derived that characterizes the fringe pattern. In one exemplary case, the radius of curvature of the cornea 60 is approximately 8.0 millimeters (mm) and the distance from the corneal vertex to the plane of the iris 80 is approximately 4 mm. (As used herein, and consistent with conventional usage, the corneal vertex corresponds to the foremost point of the cornea 60, where the cornea intersects the visual axis.) Under these circumstance, the signal strength, I, of the light reflected by the iris 80 is given by, $$I = \sin^2\left(\frac{1}{180}\pi\left(580645g\sqrt{\tan^2\left(\sin^{-1}\left(\frac{r}{8}\right) - \sin^{-1}\left(\frac{r}{8g}\right)\right)(u)^2 + (u)^2} - \right.\right.$$
$$\left.\left. 580645g\left(8 - \sqrt{\left(r - u\tan\left(\sin^{-1}\left(\frac{r}{8}\right) - \sin^{-1}\left(\frac{r}{8g}\right)\right)\right)^2 + 16}\right)\right)\right)$$

where $$u = 8\sqrt{1 - \frac{r^2}{64}} - 4,$$

g is glucose concentration, and r is the distance in the plane of the iris 80 between the visual axis 90 of the eye 10 and the point where the strength is evaluated. This expression quantifies the variation in intensity of light across region 175 of the iris 80 illuminated by the two overlapping probe beams 140, 150. More specifically, this expression characterizes the variation in intensity corresponding to the fringe pattern that results from the interference of these two beams 140, 150. Accordingly, equations such as these could be used to determine the index of refraction and the relative glucose concentration from a given fringe pattern. These equations, however, are complex and other techniques may be preferred for ascertaining the relative levels of glucose concentration.

Figure 5:
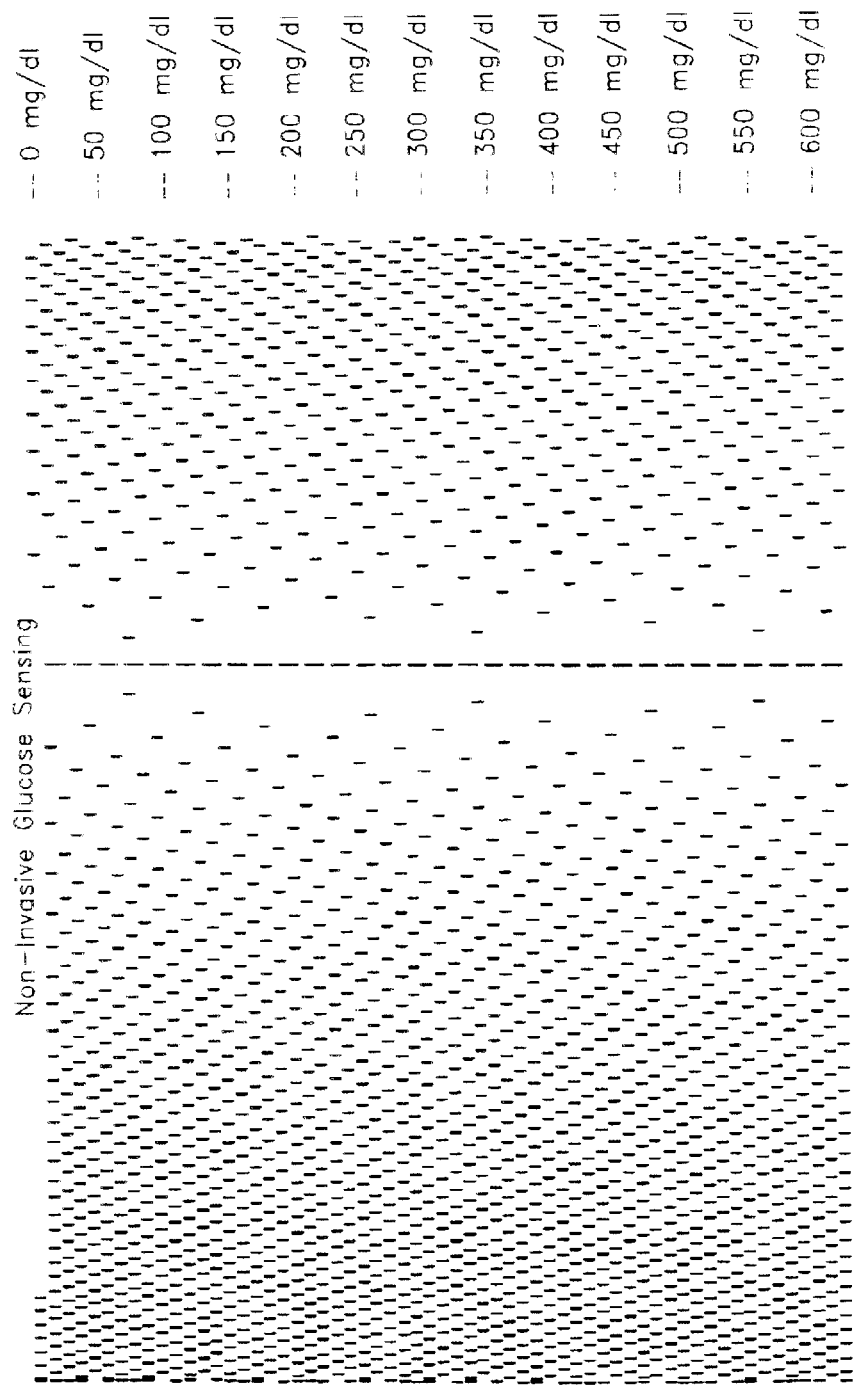
FIG. 5 illustrates how the peak locations change with refractive index over a range of glucose concentrations from zero to about 600 milligrams per deciliter (mg/dl) or about six times the typical level found in healthy human beings.

In FIG. 5, a series of plots illustrates how the peak locations move with increase in glucose concentration. The plurality of plots corresponds to a range of glucose concentrations from zero to about 600 milligram per deciliter (mg/dl), the later value of which is about six times the normal level found in healthy human beings. No two of these patterns are alike. Accordingly, analysis of the pattern yields a sensitive and substantially unambiguous reading of the refractive index over the entire range. Thus, in various preferred embodiments, the signal from the sensor 190 may be processed to determine the location of the peaks and troughs. The set of locations of the various peaks and troughs is like a fingerprint which can be used to determine the relative index of refraction and glucose concentration. In certain preferred embodiments, the pattern of peaks and troughs, i.e., their relative location and spacing with respect to each other and to the center of symmetry, can be compared to a database of similar patterns for different glucose concentrations. By looking up the pattern in electronic look-up tables, a value of the refractive index can be obtained from which the relative glucose concentration can be calculated after calibrating the instrument 100. The look-up tables may include glucose concentrations in other embodiments.

For example, in some embodiments, the signal from the sensor 190 may be digitized and sent to a computer, microprocessor, or other electronics, which determines the point of symmetry and locates the peaks and troughs within a range of this point of symmetry. For instance, peaks and troughs within about 0.5 mm of the point of symmetry can be determined. This mapping of the peaks and valleys can be compared with a set of patterns computed from analytical expressions for a range of plausible glucose levels. One or more of the computed patterns from the set that substantially matches the fringe pattern produced by the measurement can be used to arrive at the measured value of relative glucose concentration. Averaging and/or other signal processing techniques may be employed to reduce noise or otherwise improve accuracy and precision.

In other preferred embodiments, the intensity of the fringe pattern imaged on the sensor 190 can be fit to a curve, e.g., using a least squares fits or other fitting techniques. Based on the curve to which the intensity pattern is fit, unknowns such as the index of refraction or glucose concentration in the aqueous humor can be determined.

Still other techniques for ascertaining the index of refraction of the aqueous humor from the intensity pattern of the overlapping probe beams 140, 150 may be utilized, both those well known and well as those yet to be devised. Also, variations and additional processes, such as for example digital signal processing, filtering, and noise reduction techniques, may be used to yield more accurate or precise results or to simplify or accelerate the analysis.

Thus, in various embodiments, light from the two probe beams 140, 150 is diffusely reflected off the iris 80, some of that light being collected by the imaging lens 200 and focused onto the sensor 190. An image of the fringe pattern resulting from interfering the two beams 140, 150 is thereby formed on the sensor 190. The signal output from the sensor 190 is analyzed, for example, as described above, to determine the glucose concentration based on the relationship established between refractive index and glucose concentration by calibrating the instrument with independent measurements.

The profiles in the FIGS. 4 and 5 were computed using a model wherein the iris 80 was assumed to be a smooth, reflecting surface. In certain cases, however, the iris 80 is more accurately represented as a surface that is rough compared to the dimensions of the wavelength of the light from the coherent light source 115. The roughness of the iris 80 gives rise to several effects. First, the distance from the cornea 60 to different locations on the iris 80 does not change smoothly, but includes an additional random perturbation added to it. Second, when illuminated by coherent light, the iris roughness generates speckle. Speckle, which is well known in the art, is a random-appearing variation in the intensity of the reflected light that is superimposed upon or multiplied by to the underlying fringe pattern.

In certain cases, errors that may be introduced by these effects can be reduced by employing various instrument configurations and measurement techniques. For example, the optical sensor 190 may comprise a two-dimensional detector array, which detects a plurality of elongated fringes corresponding to the fringe pattern. Instead of simply obtaining a single intensity distribution across a cross-section of the fringe pattern, a plurality of such cross-sections can taken at different locations-along the length of the fringes. In this manner, the variations caused by the roughness of the iris 80 may be averaged out over the length of the fringes. For example, if the fringes are oriented substantially vertically (i.e., along the y-direction), a separate estimate of the fringe location and spacing can be produced for each horizontal scan line (i.e., along the x-direction) of the array 190. The results of averaging over several horizontal scan lines produces an average value of fringe spacing that may be more accurate than the value produced by a single horizontal scan across the array 190. The variations due to the iris 80 being a rough surface, can thereby be reduced.

Figure 6:
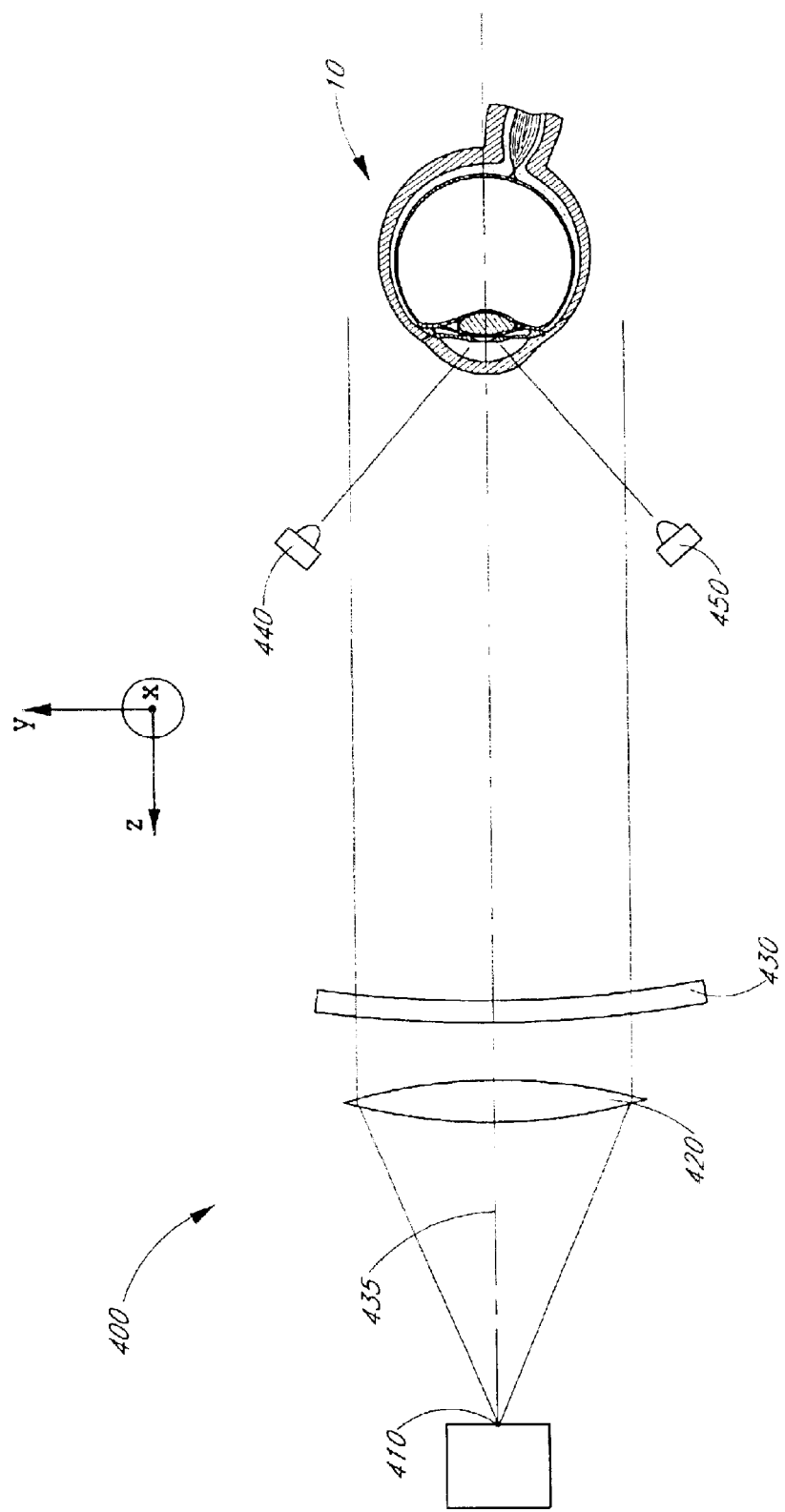
FIG. 6 schematically illustrates a subsystem used for lateral alignment of the probe beams with respect to the eye in two orthogonal directions (x, y) that are normal to the visual axis.

In certain embodiments, the device 100 additionally comprises a lateral alignment subsystem 400 schematically illustrated in FIG. 6 that is used to align the device 100 with respect to the eye 10. The subsystem 400 is preferably used for "lateral" alignment, i.e., positioning along two orthogonal axes (e.g., x, y) normal to the visual axis 90. The lateral alignment subsystem 400 comprises a central light source 410, a lens 420, and a curved mirror 430 aligned along an optical axis 435. The lateral alignment subsystem further includes two additional light sources 440, 450 offset from and on opposite sides of the optical axis 435. Other configurations and designs, however, are possible.

In one preferred embodiment, the central light source 410 comprises a light emitting diode (LED) that produces light in the green portion of the light spectrum. Green is preferred since it is easily detected by the eye, although the choice herein does not preclude the used of other colors or other types of light sources. The lateral spatial extent of the light produced by light source 410 preferably has a diameter that is relatively small in relation to other dimensions of the subsystem 400, namely the focal length of the lens 420, and approaches the characteristics of an idealized point source. A pin hole or other aperture may be included to reduce the effective spatial extent of the source of light 410.

The off-centered light sources 440, 450 may also comprise light emitting diodes LEDs but may comprise other types of light sources in other embodiments. In various preferred embodiments, the light sources 440, 450 are white light-emitting diodes that diffusely illuminate of the eye 10. The lateral spatial extent of the light produced by these two light sources 440, 450 also is preferably small in relation to other dimensions of the subsystem 400 and may approach the characteristics of an idealized point source. A pin hole or other aperture may be included to reduce the effective spatial extent of these light sources 440, 450. The two offset light sources 440, 450 are preferably arranged on opposite sides of the optical axis 435. In one preferred embodiment, the two offset light sources 440, 450 are disposed above and below the optical axis 435, in a vertical plane (e.g., the y-z plane) through the optical axis. More preferably, the two offset light sources 440, 450 are equally distant from the optical axis 435 and are also equally distant from the eye 10. In such a configuration, the two light sources 440, 450 are disposed symmetrically about the optical axis 435. Accordingly, the angle from the eye 10 to the first offset source 440, as measured with respect to the optical axis 435, is equal and opposite to the angle from the eye to the second offset source 450. Other arrangements are possible, however, the first and second offset light sources 440, 450 are preferably on opposite sides of the central light source 410 as seen by the eye 10. Preferably, the offset lights sources 440, 450 are close to the eye such that the images of these light sources move independently of the image of the green light source which appears to the eye 10 to be at infinity. For instance, the offset light sources 440, 450 may be a distance of about one inch (i.e., about 25 mm) from the cornea.

Preferably, the lens 420 comprises a collimating lens. More specifically, the lens 420 has a focal length and is positioned a distance from the central light source 410 so as to provide a substantially collimated beam that is directed toward the eye 10. In other embodiments, other types of optical elements may provide collimation such as, for example, concave mirrors and diffractive optic elements.

The curved mirror 430 is partly transparent, which may be accomplished with a partially silvered mirror 430. Some of the light from the central light source 410 therefore is transmitted through the mirror, while some of the light from the offset light sources 440, 450 is reflected as will be discussed below. Preferably, the mirror 430 is concave from the perspective of the eye 10 and of uniform thickness such that it possesses substantially zero refractive power. The use of the collimating lens 420 and the curved mirror 430 is illustrative and does not preclude the use of other optical elements in other configurations.

In certain embodiments, the subsystem 400 is used to correctly position the eye 10 laterally relative to the device 100 in two directions. This task may involve for example aligning the apparatus 100 with respect to the eye 10 vertically and horizontally. Light from the light source 410 is substantially collimated by the lens 420, is transmitted through the curved mirror 430, and enters the eye 10 through the cornea 60. Using this configuration, a patient observes a small green spot of light that is substantially centered on the optical axis 435 defined by the source 410, the lens 420.

The additional offset light sources 440, 450, which are preferably white light sources, diffusely illuminate the front of the eye 10. Some of the light from the offset light sources 440, 450 is reflected from the surface of the eye 10 to the curved mirror 430, which is approximately located at its focal distance from the eye, or more specifically from the ocular lens. This provides the patient with a view of the eye 10 that appears at optical infinity. The view includes the iris 80, pupil 75, and lids, etc. Moreover, light that is specularly reflected from the steeply convex surface of the cornea 60 forms two tiny virtual images of the offset light sources 440, 450, which appear to the patient as bright white points approximately in the plane of the iris 80. Similarly, the light from the central source 410 that is reflected from the cornea 60 appears as a tiny green point. During alignment, the patient moves laterally, e.g., horizontally and vertically, with respect to the instrument 100 that includes the alignment subsystem 400. The patient adjusts his or her lateral position until the green dot image produced by the central light source 410 is centered between the two images of the offset white light sources 440, 450. The instrument 100 is considered to be aligned in two orthogonal directions, e.g., the vertical and horizontal axes, when the images of the two light sources 440, 450 are collinear with and bisected by the green dot image produced by the central light source 410, and the green point reflected from the cornea 60 is centered on the green source 410 seen directly through the partially transparent mirror 430.

The above alignment procedure is based on an assumption that the patient's vision is approximately emmetropic, that is that the patient's eye is focused on a target at infinity and that he or she is neither nearsighted nor farsighted. If the patient were, for example, nearsighted, the image of the patient's eye 10 in the above procedure would appear defocused, as would small green spot image produced by the central light source 410. In certain embodiments, such non-emmetropic conditions may be corrected by adjusting the longitudinal position of the central light source 410 towards or away from the collimating lens 420 until the small green spot image produced by the light source 410 appears sharp to the patient. Correction may also be provided by positioning the curved mirror 430 towards or away from the patient until the image of the patient's eye appears sharp. To adjust the positioning, the subsystem 400 may further comprise, for example, micrometers or other translation devices mechanically coupled to the source 410, collimating lens 420, and/or the curved mirror 430. In this configuration, the patient adjusts the position of the source 410, collimating lens 420, and/or the curved mirror 430 by adjusting the translation devices. In other embodiments, after appropriate adjustment has been reached, e.g., once the proper non-emmetropic corrections have been made, the position is locked in place. In still other embodiments, the amount of correction can be recorded and made available so that several patients requiring different non-emmetropic correction settings may easily use the same instrument. Manual or electronic positioning and translation components can be used. In the case where positioning is by electronic apparatus, the one or more correction setting can be stored in memory and adjustment can be automatic.

In addition to providing correct lateral, e.g., horizontal and vertical, alignment, the instrument 100 is preferably located an appropriate distance away from the eye 10. Most preferably, the instrument 100 is positioned such that the focal point of the focusing lens 170 in the second arm of the interferometer 150 corresponds to the center of curvature 260 of the cornea 80.

Figure 7:
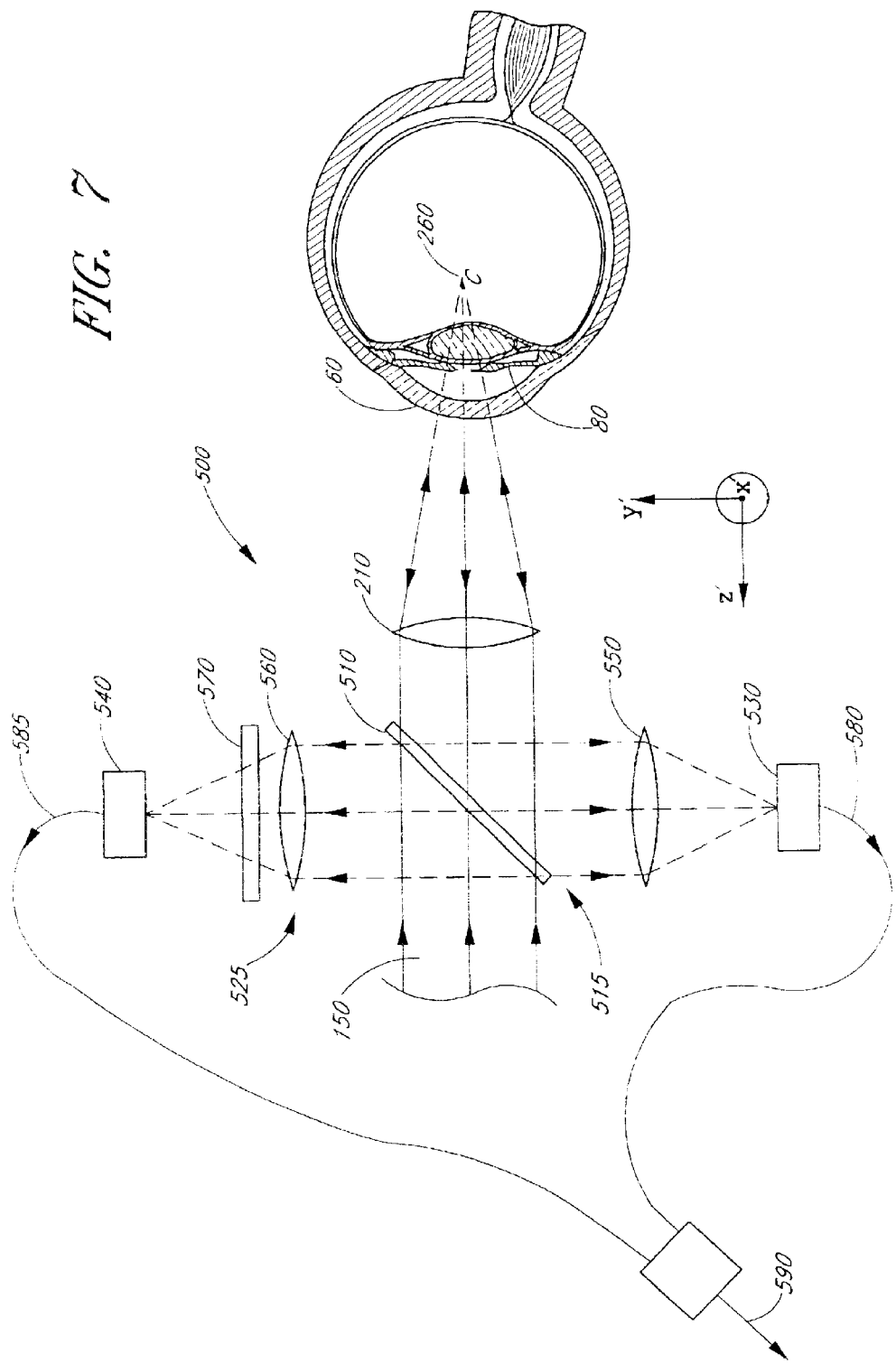
FIG. 7 schematically illustrates a side view of subsystem used for longitudinal alignment along an axis through the center of curvature of the cornea, such that the distance separating the optical system and the eye is appropriate for accurate measurement of the glucose concentration.

In certain embodiments, for example, the instrument 100 further comprises an alignment subsystem 500, such as schematically illustrated in FIG. 7, that facilitates longitudinal positioning of the instrument 100 with respect to the eye 10 as well as fine adjustment of the lateral alignment. This subsystem 500 is for establishing the appropriate distance between the optical device 100 and the eye 10. More specifically, the separation of the instrument 100 from the eye 10 as measured along an axis through the center of curvature, C, of the cornea 60 (i.e., along the z'-axis shown in FIG. 7), is preferably such that accurate measurement of the glucose concentration can be obtained. This z'-axis is preferably offset from the visual axis 90 by a small angle.

The fine longitudinal and lateral alignment subsystem 500 comprises a beamsplitter 510 which introduces two (i.e., third and fourth) additional optical paths 515, 525 into the instrument 100 and two optical detectors 530, 540, one in each of these optical paths. Two lenses 550, 560 are associated with the two detectors 530, 540 in the third and fourth optical paths 515, 525. The fine lateral/longitudinal alignment subsystem 500 further includes an optical filter 570 in the fourth path 525 for filtering light directed to the detector 540. The detectors 530, 540 respectively produce alignment and reference signals 580, 585, which together enable substantially precise longitudinal as well as lateral alignment.

The beamsplitter 510 may comprise a beamsplitter cube or a plate with a partially reflective coating formed thereon. Other types of beam separators may also be used. In certain embodiments, the detectors 530, 540 may comprise photodiodes, which preferably have a small light sensitive area. The detector 530 may further include a pinhole that is used to decrease the effective photosensitive area of the detector 530. In one preferred embodiment, the pinhole aperture is less than about 0.2 millimeters in diameter. In other embodiments, the detectors 530, 540 may comprise two dimensional sensor arrays such as CCD or CMOS detector arrays. The lenses 550, 560 focus light to a small spot on the detectors 530, 540. Other types of detectors and optical elements may be employed as well. The filter 570 may comprise a neutral density filter or other type of filter or attenuator.

The subsystem 500 for fine longitudinal/lateral alignment is inserted in the second arm of the instrument 100 such that the second probe beam 150 from the coherent light source 115 propagating towards the focusing lens 170 is received by the beamsplitter 510. A portion of the light in the second probe beam 150 is reflected by the beamsplitter 510 and is focused on a small area of the detector 540 by the associated collecting lens 560. The portion of the light in the beam 150 that is not reflected by the beamsplitter 510 is transmitted and received by the focusing lens 170 which directs the light into the eye 10. Of the light incident on the eye 10, about 3% will be specularly reflected by the outer corneal surface for a typical human eye. When the focusing lens 170 is properly aligned, the light reflected by the corneal surface propagates back toward the beamsplitter 510 along the same path by which it arrived at the cornea 30. The retroreflected light traverses substantially the same path on return because, when properly aligned, the center of curvature 260 of the cornea 30 is in the focal plane of the lens 170. Under these conditions substantially all the rays in the beam 150 are normal to the corneal surface and, therefore, propagate back along the same path.

Thus, when the instrument 100 is properly aligned, some of the light reflected by the cornea 60 is additionally directed by the beamsplitter 510 toward the detector 530. This light is focused by the lens 550 onto a small area of the detector 530 for measurement. The magnitude of the alignment signal 580 is directly related to the intensity of the spot falling on the detector 530. Preferably, proper alignment produces the highest relative intensity of the alignment signal 580 output by the detector 560. A normalized signal 590 is produced by dividing the alignment signal 580 by the reference signal 585. This reference signal 585 corresponds to a fraction of the output emitted by the coherent light source 115 that is transferred to the second probe beam 150 of the inteferometer 120. Accordingly, normalization adjusts for fluctuations in the power output of the coherent light source 110.

If the instrument 100 is not correctly aligned so that the focal point of the focusing lens 170 is not coincident with the center of curvature, C, of the cornea 60, the rays in the second probe beam 150 that are reflected off the corneal surface will have non-normal reflection angles. These retroreflected rays will therefore not follow the same path back to the lens 170 and the beamsplitter 510. The deviations will result in a spot on the detector 530 that is dimmer or one that partially or totally misses the effective photosensitive region of the detector. Under non-ideal conditions, when the longitudinal or lateral alignment is off, the normalized alignment signal 590 is correspondingly smaller than the aligned case where the alignment in all three orthogonal directions is substantially correct.

Thus, in one preferred embodiment, when the instrument 100 is properly aligned, the alignment subsystem 500 preferably produces the maximum normalized alignment signal 590. A small audio speaker may be included to emit an audio verification when the normalized signal 590 reaches its aligned value. The detector electronics can be designed to automatically capture an image of the fringes produced at the iris 80 at this time when suitable alignment is achieved.

Under preferred alignment conditions, the light in the second probe beam 150 that is reflected by the beamsplitter 510 and directed onto the reference detector 540 is more intense than the light reflected from the cornea 60. In certain embodiments, the filter 570 is used to attenuate the intensity of the light focused onto this detector 540. This filter 570 may reduce the intensity so that the reference signal 585 is approximately equal to the alignment signal 580 and the normalized signal 590 is approximately one when suitable alignment is achieved. Other methods of compensating for the higher intensity light received by the detector 540 are also possible. For example, the light incident on the detector 540 may be defocused to produce a lower value of the reference signal 585.

Figure 8:
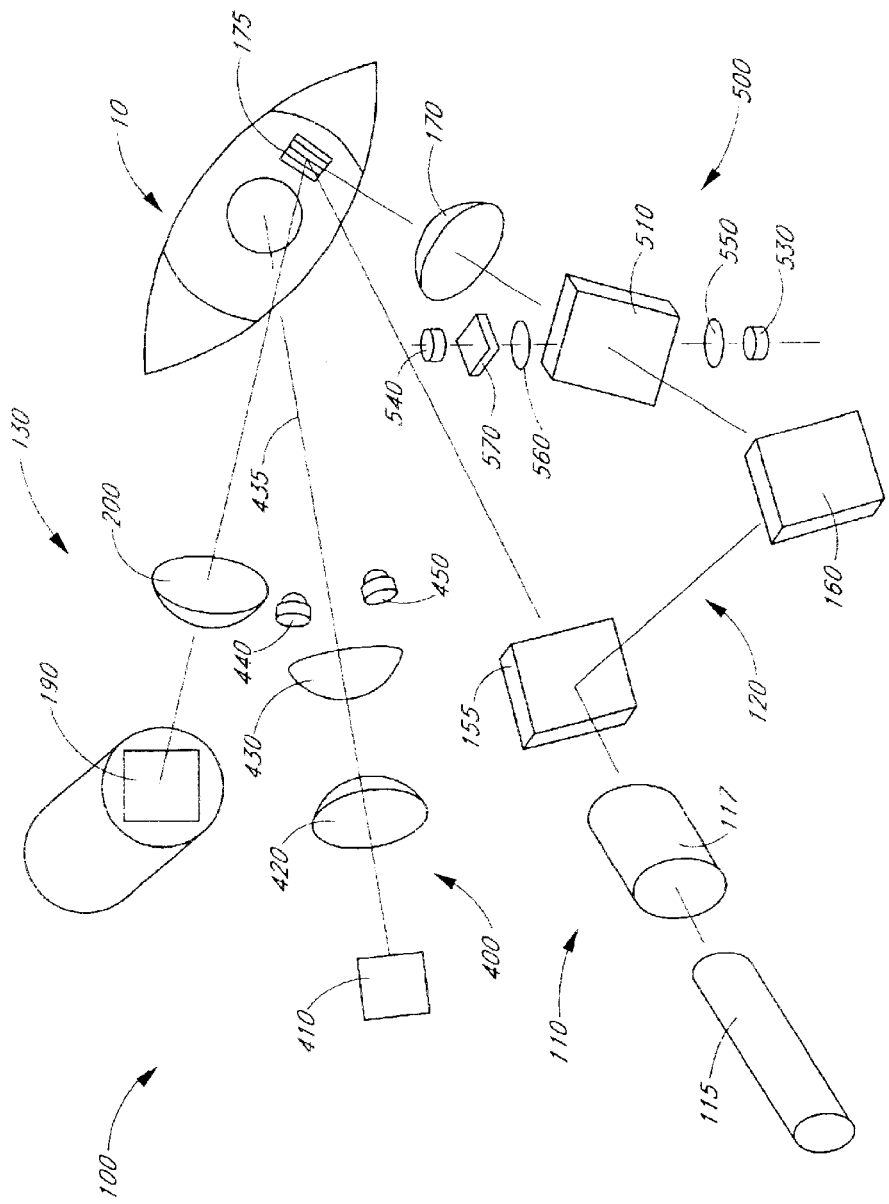
FIG. 8 schematically illustrates a system for measuring the concentration of glucose in the bloodstream of a subject together with the aligning subsystems shown in FIGS. 6 and 7.

In certain embodiments, such as schematically illustrated in FIG. 8, the device 100 for measuring the concentration of glucose in the bloodstream preferably includes both the rough lateral alignment subsystem 400 as well as the fine lateral/longitudinal alignment system 500. The lateral alignment subsystem 400 is particularly well suited for aligning the instrument 100 laterally with respect to the eye 10, i.e., in the x and y direction. The fine lateral/longitudinal alignment subsystem 500 may be utilized to position the device 100 at the appropriately in all three directions, i.e., x, y, and z. Although alignment systems 400, 500 such as those described with reference to FIGS. 6 and 7 are shown, other types of systems for aligning the instrument 100 may be employed as well. Alignment systems both well known as well as those yet to be devised are considered possible.

Figure 9:
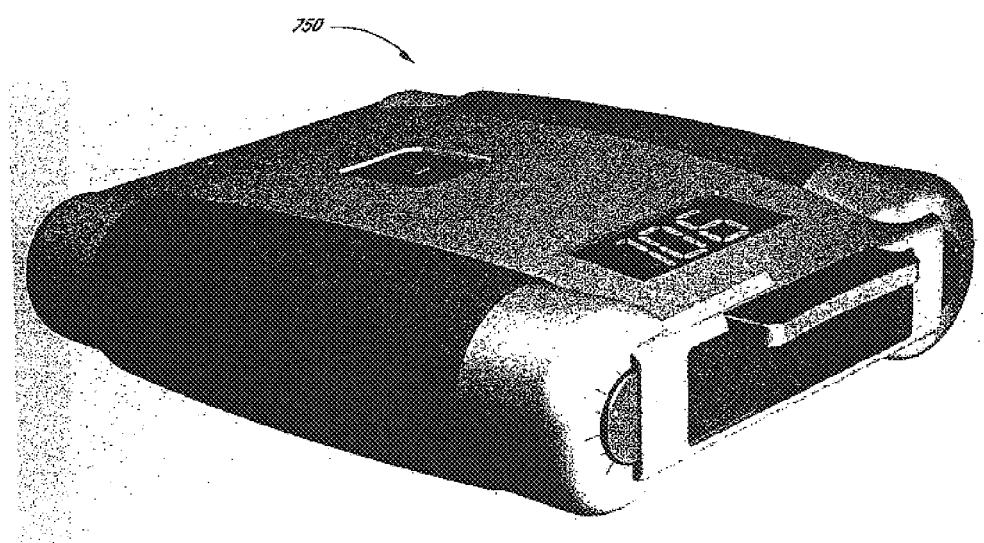
FIG. 9 is an artistic rendering of a compact instrument for measuring the concentration of glucose in the bloodstream of a subject.

In various preferred embodiments, however, substantially all the optical components are included in a common structure and may be contained within an enclosure to produce a compact instrument 750 such as illustrated in FIG. 9. In the embodiment shown in FIG. 9, the compact enclosed instrument 750 is about the size of a small book or pair of binoculars or preferably smaller. The particular design, however, should not be so restricted and may take other shapes and forms.

In certain embodiments of the device 750, the patient activates the instrument using for example a switch. The light sources 410, 440, 450, the detectors 190, 530, 540, and supporting electronic are powered. The coherent light source 115 may be set at a relatively low level. The patient then peers into an eyepiece (e.g., a window) and sees his or her eye reflected from the curved mirror 430. The patient proceeds to move the instrument 750 laterally in a plane normal to the visual axis 90, e.g., vertically and horizontally, or in two other orthogonal directions depending on the design. The patient endeavors to center the small green spot of light produced by the central light source 410 between the two images of the two offset light sources 440, 450. While maintaining alignment in the plane normal to the visual axis 90, the patient translates the instrument 750 toward or away from his or her eye 10 until an audio alignment signal is heard. The fringe pattern on the iris 80 is captured and a reading appears on a display included in the instrument 750.

As discussed above, an audio alignment signal may be triggered when the normalized alignment signal 590 is maximized. In certain embodiments, the instrument 750 may be configured such that when this condition is satisfied, the coherent light source 115 momentarily brightens. Also, one video frame or field may be captured by the detector 190. Subsequently, the coherent light source 115 is turn off or otherwise powered down and the processing or computations are performed. When the signal processing is complete, the result can be displayed.

The fringes produced at the iris 80 are not an absolute measure of glucose concentration. Fringe spacing, for example, has a slight dependence on the shape of the particular patient's eye, which, in turn, affects the various path lengths within the aqueous humor. Therefore, in certain embodiments, the devices 100, 750 are preferably calibrated to individual users. In various embodiments, such as instruments 100, 750 used by a diabetic family, a single instrument is calibrated separately for different users.

The calibration procedure may be as follows. For a period of time, e.g. a few days, the user measures blood glucose one or more times a day using one or more methods that provide an independent accurate measure of glucose concentration. Methods well known in the art such as the finger stick method may be suitable. The user also performs a measurement of the index of refraction of the aqueous humor with the instrument 100, 750 described above. The user enters the results of both readings into the device 100, 750 possibly using an interface such as a keypad that plugs into the instrument for such purposes. By storing measurements obtained over a period of time, the instrument 100, 750 can be calibrated with suitable accuracy. In various embodiments, the data are analyzed automatically and the instrument 100, 750 indicates when sufficient data have been obtained to generate a reliable calibration. The appropriate constant or set of constants can be automatically recorded by the instrument 100, 750. A display or other interface can be used to indicate that the instrument 100, 750 is properly calibrated and ready for regular use. In other embodiments, a single measurement may be employed to calibrate the instrument 100, 750 although multiple measurements may improve accuracy.

Based on the independently measured glucose levels, the values obtained by of the instrument 100 are preferably calibrated so that the output produced by the instrument can be correlated with the appropriate glucose level. As different eyes 10 are physically different, the instrument 100 is preferably calibrated separately for different patients.

Glucose, however, may not be the only substance dissolved in the aqueous humor, and these other substances may affect the index of refraction and the fringes produced on the iris 80. The effect of such substances is expected to be sufficiently small so as not to significantly alter the fringes produced on the iris 80 and interfere with accurate measurements of glucose levels. Nevertheless, the effect of such substances can be reduced or substantially eliminated by employing various techniques. For instance, the measurements can be performed at the appropriate wavelengths to reduce the effect of other solutes on the measured index of refraction. A given solute, such as for example glucose, may cause a change in refractive index that varies with the wavelength of the incident light. The variation in refractive index with wavelength is called dispersion. Different solutes have different dispersion characteristics. Therefore, in certain embodiments, a suitable wavelength can be chosen such that variations in glucose concentrations causes a significant change in the refractive index, while any interfering substances do not. For example, the concentration of sodium chloride in the aqueous humor may fluctuate. However, such changes have a negligible effect on the refractive index in the near infrared wavelengths where variations in the glucose level do significantly affect the refractive index.

In other embodiments, the measurement of the spacing and locations of the fringes produced at the iris 80 can be performed at two or more different wavelengths. Preferably, different wavelengths are selected that manifest different variations in refractive index with concentration of glucose and the interfering material. Measurements of the fringe spacing or location at these two wavelengths provides sufficient information to distinguish between the effects of the two solutes. Two measurements are performed, one at each wavelength and two values of refractive index are obtained. The glucose concentration in the aqueous humor can be determined from the two refractive index changes at the two wavelengths. In general, if there are N solutes, the contribution of one of the solutes, e.g., glucose, can be determined by measuring the fringe pattern at N properly chosen wavelengths. Other methods and variations, however, may be employed to ascertain the level of glucose concentration.

In certain cases, the physical distance between the cornea 60 and the iris 80 varies. Such variations cause the fringe pattern produced at the iris 80 to change, thus interfering with accurate refractive index measurements. Such changes in this physical distance, however, may be accounted for by various techniques.

In various embodiments, the effects of changes in the physical length of the light paths can be separated out. These optical path lengths govern in part the times required for light to travel over the physical paths. To account for variations in length, additional measurements can be obtained at different wavelengths. In one preferred embodiment, for example, a second coherent light source of different wavelength may be included in the instrument 100, 750. Preferably, the refractive index of glucose is different for the two wavelengths. Using the second coherent light source, a second set of measurements of the resulting fringe pattern can be obtained. This second set of measurements will have the same pair of physical path lengths but a different pair of optical path lengths as the index of refraction is different for the two wavelengths. Thus, the difference between the two fringe patterns is a measure of the difference in refractive indices at the two wavelengths, which, in turn, can be use to establish the physical path length. In this manner, the measurement of glucose concentration can be calibrated for varying thicknesses between the cornea 60 and the iris 80.

Other variations of the instrument design and configuration are considered possible. For example, instead of using a video camera, the image of the fringes could be swept across a vertical slit or set of slits in front of one or more photodetectors, thus converting the fringe spacing into temporal frequencies that could be measured. The alignment might also be performed entirely automatically, using, for example, a video image of the eye and corneal reflection to drive motors that position the optical system with respect to the eye. The instrument may also be interfaced to a computer as well. Still other variations of the instrument and techniques for measuring glucose concentration may be employed. The methods and designs should not be limited only to those embodiments disclosed herein.

Those skilled in the art will appreciate that the methods and designs described above have additional applications and that the relevant applications are not limited to those specifically recited above. Also, the present invention may be embodied in other specific forms without departing from the essential characteristics as described herein. The embodiments described above are to be considered in all respects as illustrative only and not restrictive in any manner.

What is claimed is:

1. A method of measuring glucose levels in blood of a living being having an eye comprising a cornea and a lens, which together form an anterior chamber, said eye further comprising an iris and aqueous humor in said anterior chamber, said aqueous humor having an index of refraction correlated to said glucose level in said blood, said method comprising:
   propagating two substantially coherent beams of light through said cornea to illuminate a region of said iris, said two substantially coherent beams of light propagating through said aqueous humor to reach said iris;
   overlapping said two beams on said region of said iris, said two beams being sufficiently coherent so as to produce an interference pattern in said region of said iris, said interference pattern comprising a plurality of fringes having a spatial arrangement that depends on said index of refraction of said aqueous humor;
   imaging said interference pattern onto a light sensitive optical detector; and
   determining said glucose level in said blood from said spatial arrangement of said fringes in said interference pattern.

2. The method of claim 1, wherein said glucose level is determined at least in part by identifying the locations of extrema in said spatial arrangement of said fringes.

3. The method of claim 1, wherein said glucose level is determined at least in part from the fringe spacing.

4. The method of claim 1, wherein said glucose level is determined at least in part by fitting at least a cross-sectional profile of said fringe pattern to a curve.

5. The method of claim 1, wherein said glucose level is determined at least in part by matching a profile of said fringe patterns to known profiles in a look-up table.

6. An apparatus for monitoring glucose fluctuations by measuring properties of an eye, said apparatus comprising:
   a light source which emits a beam of light;
   an optical element situated to receive said beam of light from said light source and to split said beam of light into first and second probe beams that propagate along respective first and second optical paths;
   at lease one optical element in one of said optical paths to alter said optical path such that first and second probe beams intersect at a target plane;
   an optical detector and imaging optics for imaging said target plane on said optical detector;
   an alignment system for aligning said first and second probe beams with said eye, said alignment system including an optical sensor having an electronic output indicative of the state of alignment; and
   an alignment system for aligning said first and second probe beams with said eye, said alignment system including an optical sensor having an electronic output indicative of the state of alignment; and
   electronics electrically coupled to (i) said electronic output of said optical sensor included in said alignment system and to (ii) said optical detector that images said target plane, said electronics configured to cause said optical detector to capture an image of said target plane based on said state of alignment.

7. The apparatus of claim 6, wherein said light source comprises a laser.

8. The apparatus of claim 6, wherein said optical element situated to receive said beam of light from said light source comprises a beamsplitter.

9. The apparatus of claim 6, wherein said at least one optical element that alters said optical path such that said first and second probe beams intersects comprises a mirror.

10. The apparatus of claim 6, wherein said imaging optics includes a lens.

11. The apparatus of claim 6, further comprising focusing optics in said second optical path that transforms said second optical beam into a converging beam.

12. The apparatus of claim 11, wherein said eye includes a cornea having a curved outer surface defined by a center of curvature and said focusing optics configured and situated to transform said second optical beam into a converging beam comprising wavefronts having a center of curvature substantially coincident with the center of curvature of said outer surface of said cornea.

13. The apparatus of claim 6, wherein said optical detector and said imaging optics are arranged together with said target plane to satisfy the Scheimpflug condition.

14. A method of monitoring glucose levels in blood of a living being having an eye, said method comprising:
   propagating light through a portion of said eye comprising aqueous is humor having an index of refraction that varies with glucose concentration;
   obtaining phase information associated with said light through optical interference, said phase information depending at least in part on said index of refraction of said aqueous humor; said step of obtaining phase information comprising analyzing interference fringes.

15. The method of claim 14, further comprising correlating said phase information with at least one independently measured glucose level of said living being to provide calibration.

16. An apparatus for monitoring glucose fluctuations by measuring properties of an eye said apparatus comprising:
   a light source which emits a beam of light;
   an optical element situated to receive said beam of light from said light source and to split said beam of light into first and second probe beams that propagate along respective first and second optical paths;
   focusing optics in said optical path that transforms said second optical beam into a converging beam;
   at least one optical element in one of said optical paths to alter said optical path such that first and second probe beams intersect at a target plane;
   an optical detector and imaging optics for imaging said target plane on said optical detector; and
   said eye including a cornea having a curved outer surface defined by a center of curvature and said focusing optics being configured and situated to transform said second optical beam into a converging beam comprising wavefronts having a center of curvature substantially coincident with the center of curvature of said outer surface of said cornea.

17. The apparatus of claim 16, wherein said optical detector and said imaging optics are arranged together with said target plane to satisfy the Scheimpflug condition.

* * * * *